United States Patent [19]

Rittersdorf et al.

[11] 4,260,777

[45] Apr. 7, 1981

[54] DIAGNOSTIC AGENT FOR THE DETECTION OF PROTEIN IN BODY FLUIDS

[75] Inventors: Walter Rittersdorf, Mannheim-Waldhof; Werner Güthlein, Mannheim-Neckarau; Wolfgang Werner, Mannheim-Vogelstang; Hanz-Georg Rey; Peter Rieckmann, both of Mannheim-Waldhof, all of Fed. Rep. of Germany

[73] Assignee: Boehringer Mannheim GmbH, Fed. Rep. of Germany

[21] Appl. No.: 740,462

[22] Filed: Nov. 10, 1976

Related U.S. Application Data

[62] Division of Ser. No. 661,687, Feb. 26, 1976, Pat. No. 4,013,416.

[30] Foreign Application Priority Data

Mar. 12, 1975 [DE] Fed. Rep. of Germany ....... 2510633

[51] Int. Cl.$^3$ .......................................... C07D 327/04
[52] U.S. Cl. .................................. 549/33; 23/230 B; 252/408; 424/7
[58] Field of Search ....................... 260/327 S; 549/33

[56] References Cited

U.S. PATENT DOCUMENTS 1,786,611  12/1930  Harden ............................ 260/327 S

FOREIGN PATENT DOCUMENTS 2432388  5/1974  Fed. Rep. of Germany ....... 260/327 S Primary Examiner—John D. Randolph
Attorney, Agent, or Firm—Sprung, Felfe, Horn, Lynch & Kramer

[57] ABSTRACT

Protein in body fluids, e.g., urine, is detected by contacting a sample of the body fluid with a diagnostic agent comprising an absorbent carrier impregnated with a pH indicator of the octahalosulfophthalein group, a buffer, and at least one linear or branched chain polypropylene glycol immiscible with water; the resulting test papers are highly sensitive to protein without being subject to interfering effects by nitrogen-containing compounds.

1 Claim, No Drawings

DIAGNOSTIC AGENT FOR THE DETECTION OF PROTEIN IN BODY FLUIDS

This is a division of application Ser. No. 661,687 filed Feb. 26, 1976, now U.S. Pat. No. 4,013,416 granted Mar. 22, 1977.

The present invention is concerned with a diagnostic agent for the detection of protein in body fluids.

The detection of protein in body fluids, especially in urine, is of outstanding importance in the diagnosis of kidney diseases. Consequently, rapid diagnostic agents for the detection and determination of protein in urine have already been developed some time ago. These agents are usually test papers which have been impregnated with a buffer substance and with a so-called protein error indicator. Protein error indicators are pH indicators, the pK value of which is displaced in the presence of protein. Depending upon the direction in which the pK value is displaced by protein, the buffer present must give a pH value which lies above or below the pK value and preferably just outside the color change region of the indicator. Those indicators are preferred which, upon dipping into a protein-free urine, are present in the less colored form so that the presence of protein leads to a more or less complete change-over of the indicator into the more strongly colored form and thus gives a sensitive color change. The best known of these protein error indicators are tetrabromophenolphthalein ethyl ester and tetrabromophenol blue (octabromophenolsulphophthalein). Such protein test papers are described in the literature and, in general, permit sensitive protein detection.

However, all the known test papers suffer from the serious disadvantage that they react with the metabolites of pharmaceuticals which frequently occur in the urine, for example, of quinine, quinidine, chloroquine and other nitrogen-containing compounds, in the same way as with protein.

The present invention provides test paper in which disturbance by such interfering nitrogen-containing compounds is eliminated or reduced to negligible proportions, without impairment of the detection sensitivity for protein in comparison with the known test papers.

The invention provides a diagnostic agent for the detection of protein in body fluids, comprising an absorbent carrier impregnated with a pH indicator exhibiting protein error, which indicator is selected from the octahalosulfophthalein group, together with an appropriate buffer and at least one linear or branched chain polypropylene glycol which is immiscible with water and which optionally contains other lower oxyalkylene groups.

The absorbent carrier is preferably filter paper but other materials, such as fibre fleece, asbestos or the like, can also be used.

The polypropylene glycols to be used according to the present invention are, in particular, the linear polypropylene glycols, as well as block polymers of propylene oxide and ethylene oxide and also branched chain compounds in which propylene oxide is polymerized on to polyhydroxy alcohols, for example trimethylolpropane, glycerol or pentaerythritol, and which can possibly be modified with ethylene oxide. These polypropylene glycols must have a molecular weight of from about 500 to about 10,000.

Polypropylene glycols of this type are known and are used technically for a large variety of purposes, for example, as lubricants, hydraulic fluids, solvents, raw materials for the production of polyurethanes, wetting agents and the like.

The effect exerted by these polypropylene glycols in the diagnostic agent according to the present invention was not to have been foreseen and is also most surprising because the water-soluble representatives of this group of compounds, for example polypropylene glycol with a molecular weight of about 400 or pure polyethylene glycols do not act in the desired manner.

It is noteworthy that test papers with the desired properties can be produced with the polypropylene glycols to be used according to the present invention only with protein error indicators of the octahalosulfophthalein group. In the case of other protein error indicators, for example tetrabromophenolphthalein ethyl ester, test papers are obtained which may not react with nitrogen bases but in which the reaction with protein is also very considerably weakened. As indicators, there can, according to the present invention, be used, for example, the following: octabromophenol-sulfophthalein (tetrabromophenol blue), octachlorophenol-sulfophthalein (tetrachlorophenol blue), as well as the mixed halogenated analogues, for example, 3',3'',5',5''-tetrabromophenol-3,4,5,6-tetrachlorosulfophthalein 3',3'',5',5''-tetrachlorophenol-3,4,5,6-tetrabromosulfophthalein and 3',3''-dichloro-5',5''-dibromophenol-3,4,5,6-tetrachlorosulfophthalein.

Whereas the first three compounds are known from the literature, the other indicators are new: however, they can be prepared according to known methods, for example, by the reaction of the known tetrahalobenzene sulfocarboxylic anhydrides with phenol or 2-halophenols in the presence of Lewis acids, for example tin tetrachloride, and chlorination or bromination of the resultant phenolsulfophthaleins in inert solvents, for example with chlorine or bromine in glacial acetic acid.

Those indicators are especially preferred which have four chlorine atoms in the 3',3'',5',5''-position because they are even less disturbed by nitrogen bases than the corresponding bromo compounds.

Protein test papers need a strong buffer which keeps the pH value constant even when the test papers are dipped into body fluids which possibly have a different pH value so that a change of the indicator clearly depends upon a displacement of the pK value due to protein and not upon a change of the pH value. Generally speaking, in the case of sulphophthalein indicators, the buffer is adjusted to a pH value which lies somewhat below the pH change region of the indicator in order that the indicator is present completely in the less colored acidic form. However, a better sensitivity towards very small concentrations of protein are obtained when the pH value of the buffer lies in the change region of the indicator. However, the result of this is that, after dipping into urine, a part of the indicator already changes and the negative coloration is more difficult to differentiate from a slight protein coloration.

However, a further unexpected property of the polypropylene glycols used according to the present invention is that they suppress this commencing indicator change without substantially influencing the sensitivity towards protein.

By the "change region" of an indicator, there is to be understood, in general, the pH region of, in each case, one unit above and below the pK value in pure water.

For the protein test papers according to the present invention, pH values are preferably selected which lie about 1.0 units below up to about 0.5 units above the pK value of the indicators employed. Since these lie in the region of 3.5 to 4.0, the usable pH range extends from about pH 2.5 to about pH 4.5. In the case of lower values, a weakening of the protein reaction generally occurs and in the case of higher values a strengthening of the reaction with the nitrogen bases and with normal urine. The preferred pH value, which depends not only upon the indicator used but also upon the nature of the polypropylene glycol used according to the present invention and upon the other reagents present, is easily determined by simple serial experiments in which the pH value and the amount of the buffer is so varied that the indicator, upon dipping into protein-free urine, still just shows a pure "acid" color.

As buffers, there can be used all those which, in the said range, possess a good buffering capacity, for example, mixtures of citric acid, malic acid, tartaric acid and the like with their alkali metal or ammonium salts.

Although some of the polypropylene glycols used according to the present invention possess surface-active properties, it can, nevertheless, be desirable to add conventional tensides for the purpose of better distribution. For this purpose, it is particularly preferred to use wetting agents, especially ethoxylated fatty alcohols and phenols containing 1 to 4 oxyethylene groups. Anionic wetting agents strengthen the reaction with the nitrogen bases, whereas cationic tensides bring about a strong falsely positive indicator reaction if they are not used in conjunction with very acidic buffers which inhibit the protein reaction. Therefore, these two classes of tensides are not suitable.

Swelling materials and thickening agents can also be present, which retard the bleeding out of the reagents from the wettened test paper. However, it might be necessary to test whether these are compatible with the buffer substances used. Thus, for example, hydroxyethyl- and hydroxypropylcellulose have proved to be useful.

Furthermore, complex forming agents, especially magnesium sulfate, can be added to the reagents.

The polypropylene glycols used according to the present invention, as well as the other components, can be employed in the following amounts, referred to 100 ml. of impregnation solution:

polypropylene glycol to be used according to the present invention: 0.5 to 5 g., preferably 1 to 2 g.; buffer 10 to 30 g., preferably 15 to 20 g.; indicator 0.02 to 0.2 g., preferably 0.05 to 0.1 g.; surface-active adjuvant 0.0 to 1.0 g., preferably 0.2 to 0.5 g.

As solvents for the components, there can be used mixtures of water and lower alcohols in which all the components are soluble. However, the absorbent carrier can also be first impregnated with an aqueous buffer solution and thereafter with a solution of the other components in an organic solvent.

The best papers obtained can be used as such or can be stuck in known manner on to handles or, preferably, can be sealed between synthetic resin films and finemesh materials.

The following Examples are given for the purpose of illustrating the present invention, the effectiveness with regard to the influence of nitrogen bases being illustrated in that the amount of quinine is given the coloration of which simulates a content of 5 mg.% albumin (upper limit of normal excretion). Thus, the greater is this amount, then the less is the test disturbed by quinine. The disturbance due to other nitrogen bases, for example, quinidine, chloroquine, benzydamine and the like, is of the same order of magnitude as that of quinine.

EXAMPLE 1

Filter paper (Schleicher & Schüll 2316) was successively impregnated with the following two solutions and, after each impregnation, dried at 60° C.:

| Solution 1: | | |
|---|---|---|
| Citric acid monohydrate | | 20 g. |
| ammonia, 25% aqueous solution | about | 10 ml. |
| distilled water | ad | 100 ml. |
| The solution is adjusted to a pH value of | | 4.1. |
| Solution 2: | | |
| 3',3'',5',5''-tetrachlorophenol-3,4,5,6-tetrabromosulfophthalein (pK = 3.9) | | 50 mg. |
| polypropylene glycol, average molecular weight 1200 (polyglykol P 1200) | | 2 g. |
| methanol | ad | 100 ml. |

The test papers gave a yellow reaction with normal urine and with albumin-containing urines gave green to blue-green coloration of increasing intensity.

Urines with a quinine content of about 100 mg.% gave the same green coloration as urine with 5 mg.% albumin.

A test paper with the same composition but without the polypropylene glycol gave a green reaction with normal urine. The green coloration of 5 mg.% albumin cannot be differentiated with certainty from this negative coloration. Therefore, comparison was carried out with the reaction of 25 mg.% albumin: even about 25 mg.% quinine simulate this amount of protein.

In the case of commercially available rapid tests, even 2-5 mg.% quinine simulate the presence of 5 mg.% albumin.

EXAMPLE 2

Filter paper (Schleicher & Schüll 2316) was successively impregnated with the following two solutions and dried at 60° C.:

| Solution 1: | | |
|---|---|---|
| citric acid monohydrate | | 20 g. |
| ammonia, 25% aqueous solution | about | 6 ml. |
| distilled water | ad | 100 ml. |
| The solution is adjusted to a pH value of | | 3.1 |
| Solution 2: | | |
| 3',3'',5',5'',3,4,5,6-octabromophenol-sulfophthalein (tetrabromophenol blue) (pK = 3.6) | | 50 mg. |
| polypropylene glycol, average molecular weight 2000 (Polyglykol P 2000) | | 1 g. |
| nonyl-phenol, etherified with 1-2 oxyethylene radicals (Antarox CO 210) | | 0.4 g. |
| methanol | as | 100 ml. |

These two solutions can also be made with half the amounts of solvent and combined before impregnation.

The test paper gave a yellow reaction with normal urine and with albumin-containing urines gave green colorations of increasing intensity.

Urines with a quinine content of about 50 mg.% gave the same greenish colorations as urines with 5 mg.% albumin.

A test paper with the same composition but without the polypropylene glycol gave a pale greenish reaction with normal urine.

About 10 mg.% quinine simulate, in the cases of this test paper, 5 mg.% albumin.

If, instead of the nonyl phenol etherified with 1–2 oxyethylene radicals (Antarox CO 210), there was used 0.4 g. coconut alcohol etherified with 2 oxyethylene radicals (Genapol C 020) or 0.2 g. tributyl phenol etherified with 4 oxyethylene radicals (Sapogenate T 040), then practically identical test papers were obtained.

EXAMPLE 3

Filter paper (Schleicher & Schüll 2316) was first impregnated with a 15% aqueous solution of sodium dihydrogen citrate (pH 3.5) and dried at 60° C. It was then impregnated with one of the following solutions and dried at 60° C.:

| a | 3′,3″,5′,5″,3,4,5,6-octachlorophenol-sulfophthalein | 50 mg. |
|---|---|---|
| | propylene glycol (see following Table) | 1 g. |
| | methanol | ad 100 ml. |

The properties of these test papers correspond substantially to those of Example 1.

| b | 3′,3″-dibromo-5′,5″-dichlorophenol-3,4,5,6-tetrachlorosulfophthalein | 50 mg. |
|---|---|---|
| | Desmophen 7200 | 1 g. |
| | methanol | ad 100 ml. |

The properties of these test papers correspond substantially to those of Example 2.

| c | 3′,3″,5′,5″-tetrabromophenol-3,4,5,6-tetrachlorosulfophthalein | 50 mg. |
|---|---|---|
| | Desmophen 7200 | 1 g. |
| | methanol | ad 100 ml. |

The properties of these test papers correspond substantially to those of Example 2.

TABLE

| commercial name | chemical composition according to the manufacturer | average mol. wt. | hydroxyl number |
|---|---|---|---|
| Polyglykol P 4000 | linear polypropylene glycol | 4000 | |
| Desmophen 7200 | branched polypropylene glycol modified with ethylene oxide | 3800 | about 42 |
| Desmophen 7100 | branched polypropylene glycol modified with ethylene oxide | 3100 | about 49 |
| Desmophen 3800 | partially branched polypropylene glycol | 3500 | about 46 |
| Desmophen 3400 | branched polypropylene glycol modified with ethylene oxide | 3000 | about 56 |
| Pluracol TPE 6542 | branched polypropylene glycol based on trimethylolpropane modified with ethylene oxide | 6300 | about 27 |
| Pluracol TP 2540 | branched polypropylene glycol based on trimethylolpropane | 2600 | about 64 |
| Pluracol MK 73 | branched polypropylene glycol based on glycerol | 3800 | about 29 |
| Pluracol MK 92 | branched polypropylene glycol based on trimethylolpropane | 4500 | about 37 |
| Pluronic L 101 | linear polypropylene glycol modified with ethylene oxide up to an amount of 10% | 3800 | |

EXAMPLE 4

Filter paper (Schleicher & Schüll 2316) was successively impregnated with the following two solutions and dried at 60° C.:

| Solution 1: | | |
|---|---|---|
| malic acid | | 15 g. |
| 6N aqueous sodium hydroxide solution about | | 16 ml |
| hydroxyethylcellulose (Natrosol 250 G) | | 2 g. |
| distilled water | ad | 100 ml. |
| The solution was adjusted to a pH value of | | 3.5. |
| Solution 2: | | |
| tetrabromophenol blue | | 0.6 g. |
| polyglycol P 1200 | | 3 g. |
| chloroform | ad | 100 ml. |

The properties of this test paper correspond substantially to those of Example 2.

EXAMPLE 5

3′,3″-Dichlorophenol-3,4,5,6-tetrachlorosulfophthalein 25.7 g. (0.2 mol) o-chlorophenol were mixed with 45 g. (0.14 mol) tetrachloro-o-sulfobenzoic anhydride, 9 ml. (20.4 g.) tin tetrachloride were added thereto and the reaction mixture was heated for 12 hours, while stirring, on an oil bath at 120°–130° C. Thereafter, excess chlorophenol was removed with steam and the residue was purified by repeatedly dissolving in 4 N aqueous sodium carbonate solution and precipitating with hydrochloric acid and finally recrystallized from glacial acetic acid. There were obtained 5.3 g. (47% of theory) pink colored 3′,3″-dichlorophenol-3,4,5,6-tetrachlorosulfophthalein which contains 1 mol acetic acid of crystallization; m.p. 244°–245° C. (molecular weight: $C_{19}H_8Cl_6O_5S \cdot C_2H_4O_2 = 621.13$).

In the same manner but with the use of o-bromophenol instead of o-chlorophenol, there was obtained 3′,3″-dibromophenol-3,4,5,6-tetrachlorosulfophthalein which, after recrystallization from glacial acetic acid, also contains 1 mol acetic acid of crystallization; m.p. 172°–173° C.

EXAMPLE 6

3′,3″-Dibromophenol-3,4,5,6-tetrachlorosulfophthalein 4.9 g. (0.01 mol) phenol-3,4,5,6-tetrachlorosulfophthalein were dissolved in 50 ml. glacial acetic acid and a solution of 1.1 ml. (3.37 g.) bromine (0.04 g. atom) in 50 ml. glacial acetic acid added thereto dropwise at 20° C., while stirring. Stirring was thereafter continued for 3 hours. The crystals formed were filtered off with suction and recrystallized from glacial acetic acid. There were obtained 3.9 g. (55% of theory) 3′,3″-dibromophenol-3,4,5,6-tetrachlorosulfophthalein; m.p. 173°–174° C. The compound contains 1 mol acetic acid of crystallization (molecular weight: $C_{19}H_8Br_2Cl_4O_5S \cdot C_2H_4O_2 = 710.05$).

EXAMPLE 7

3′,3″-Dibromo-5′,5″-dichlorophenol-3,4,5,6-tetrachlorosulfophthalein 3.55 g. (0.005 mol) 3′,3″-dibromophenol-3,4,5,6-tetrachlorosulfophthalein were suspended in 50 ml. glacial acetic acid. To this suspension was slowly added, while stirring, a solution of 0.94 g. (0.025 g. atom) chlorine in 50 ml. glacial acetic acid. After stirring for several hours, there were obtained 3.8 g. (90.5% of theory) of colorless crystals of 3',3''-dibromo-5',5''-dichlorophenol-3,4,5,6-tetrachlorosulfophthalein; m.p. 265°–268° C. The compound crystallizes with 2 mol acetic acid of crystallization (molecular weight: $C_{19}H_6Br_2Cl_6O_5S.2C_2H_4O_2 = 839.01$).

The same compound can also be prepared by the bromination of 3',3''-dichlorphenol-3,4,5,6-tetrachlorosulfophthalein (obtainable by the chlorination of phenol-3,4,5,6-tetrachlorosulfophthalein). The yield is 60% of theory.

EXAMPLE 8

3',3'',5',5''-Tetrachlorophenol-3,4,5,6-tetrabromosulfophthalein 13.8 g. (0.02 mol) phenol-3,4,5,6-tetrabromosulfophthalein were suspended in 100 ml. glacial acetic acid and, while stirring, a solution of 3.6 g. chlorine (about 0.1 g. atom) in 30 ml. glacial acetic acid was added dropwise at ambient temperature. The reaction mixture was thereafter stirred for several hours and the beige-colored crystals formed were filtered off with suction. After crystallization thereof from glacial acetic acid/water (9:1), there were obtained 11 g. (58.3% of theory) 3',3'',5',5''-tetrachlorophenol-3,4,5,6-tetrabromosulfophthalein in the form of colorless crystals; m.p. 203°–204° C. (decomp.). The compound crystallizes with 2 mole acetic acid of crystallization and 1 mole water of crystallization (molecular weight: $C_{19}H_6Br_4Cl_4O_5S.2CH_3COOH.H_2O = 945.9$).

In an analogous manner, from phenol-3,4,5,6-tetrachlorosulfophthalein there was obtained, by chlorination in glacial acetic acid, 3',3'',5',5''-tetrachlorophenol-3,4,5,6-tetrachlorosulfophthalein; m.p. 277°–278° C. The compound crystallizes with 1 mole acetic acid of crystallization (molecular weight: $C_{19}H_6Cl_8O_5S.C_2H_4O_2 = 690$).

It will be understood that the specification and examples are illustrative but not limitative of the present invention and that other embodiments within the spirit and scope of the invention will suggest themselves to those skilled in the art.

What is claimed is:

1. 3',3'',5',5''-Tetrachlorophenol-3,4,5,6-tetrabromosulfophthalein.

* * * * *